United States Patent [19]

Moore et al.

[11] 4,017,519
[45] Apr. 12, 1977

[54] FLUORO DIOXOLANE ANESTHETIC COMPOUNDS

[75] Inventors: George L. Moore, South Plainfield; Ross C. Terrell, Plainfield, both of N.J.

[73] Assignee: Airco, Inc., Montvale, N.J.

[22] Filed: Sept. 24, 1975

[21] Appl. No.: 616,351

Related U.S. Application Data

[62] Division of Ser. No. 348,407, April 5, 1973, Pat. No. 3,930,013, which is a division of Ser. No. 168,401, Aug. 2, 1971, Pat. No. 3,749,793.

[52] U.S. Cl. ............................................. 260/340.9
[51] Int. Cl.² ........................................ C07D 317/10
[58] Field of Search ............................... 260/340.9 R

[56] References Cited

UNITED STATES PATENTS 3,699,145  10/1972  Sianesi et al. ............... 260/340.9 X
3,795,682  3/1974   Delavarenne .................. 260/340.9

OTHER PUBLICATIONS

Larsen, Fluorine Chemistry Reviews, vol. 3, 1969, pp. 1 and 39.

*Primary Examiner*—Ethel G. Love
*Attorney, Agent, or Firm*—Roger M. Rathbun; Edmund W. Bopp; Larry R. Cassett

[57] ABSTRACT

Cyclic ether compounds of the formula

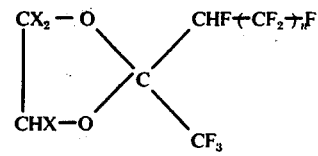

wherein $n$ is zero or one, and each X is F when $n$ is zero and is H when $n$ is one, are useful as inhalation anesthetics.

3 Claims, No Drawings

FLUORO DIOXOLANE ANESTHETIC COMPOUNDS

This is a division of application Ser. No. 348,407, filed April 5, 1973, now U.S. Pat. No. 3,930,013, issued Dec. 10, 1975, which in turn was a division of application Ser. No. 168,401, filed Aug. 2, 1971, now U.S. Pat. No. 3,749,793, issued July 31, 1973.

This invention relates to certain cyclic ether compounds and their use in producing anesthesia in anesthetic-susceptible mammals.

The compounds of the present invention have the formula

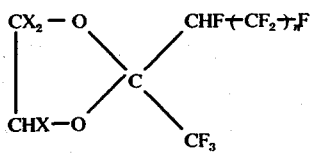

wherein $n$ is zero or one, and each X is F when $n$ is zero and is H when $n$ is one. These compounds lend themselves to effective use as inhalant anesthetics in respirable mixtures containing life-supporting concentrations of oxygen, with or without other inhalation anesthetics, such as nitrous oxide. Administration the compounds may be by any of the well known techniques for administering general inhalation anesthetics, for example by using the open drip, semi-closed or closed systems.

The effective amounts of the compounds of this invention to be employed depend on the level of anesthesia to which the mammal is to be brought, the rate at which anesthesia is to be induced, and the length of time over which anesthesia is to be maintained. Very minor volume percentages of the compounds in oxygen can often be employed. The amount used should be sufficient to provide a significant anesthetic effect, but not so much as to produce unacceptable deleterious side effects. Vapor concentrations at which the compounds of this invention may often be used are about 0.4 to 1 volume percent, with the concentration actually employed depending on the choice of anesthetic; for instance, 2,2(ethylenedioxy)-3-hydroperfluorobutane may often be used in an amount of about 0.4 to 0.6% and 2-difluoromethyl-2-trifluoromethyl-4,4,5-trifluoro-1,3-dioxolane may often be used in an amount of about 0.5 to 1%. The amount of anesthesia to be used can be regulated, starting with a small amount of the ether and gradually increasing the amount until the desired plane of anesthesia is reached. By then monitoring the physical reactions of the mammal, as is the usual procedure, the duration and plane of anesthesia can be readily controlled.

The compounds of this invention are also easily miscible with other organic liquids, including fats and oils, and have useful solvent properties, for example as solvents for fluorinated olefins and other fluorinated materials, such as fluoro waxes. The compounds of this invention may be used to prepare pastes and dispersions of such materials useful for coatings and the like, and may be used as degreasing agents. In the latter capacity, for example, the ether compounds of this invention can be used as solvents to remove grease or other oily substances from a metal surface that is to be painted.

The following examples illustrate the preparation of the compounds of the present invention.

EXAMPLE I

This example illustrates the preparation of 2,2(ethylenedioxy)-3-hydroperfluorobutane.

Sodium (20 g.) was dissolved in ethylene glycol (250 cc.) and reacted in a one-liter autoclave at 50° C. with 170 g. of commercially obtained perfluorobutene-2 ($CF_3CF=CFCF_3$) that was added via a pressure burette. The crude product (70 g.) was steam distilled and redistilled at 100 mm. Hg. to give 45 g. of 2,2(ethylenedioxy)-3-hydroperfluorobutane.

Calculated for $C_6H_5F_7O_2$: F, 55.0. Found: F, 55.0.

This normally liquid ether has a boiling point of 126° C., a specific gravity of 1.5, a vapor pressure at 25° C. of 15 mm. Hg., a refractive index ($n_D^{20}$) of 1.3265, and a not unpleasant odor. The compound is nonflammable.

EXAMPLE II

This example illustrates the preparation of 2-difluoromethyl-2-trifluoromethyl-4,4,5-trifluoro-1,3-dioxolane.

2-Difluoromethyl-2-trifluoromethyl-1,3-dioxolane (50 g.) was placed in a 500 ml. flask along with 1,2,2-trifluoroperchloroethane (Freon 113) (425 ml.) and the solution cooled to −20° C. The mixture was fluorinated with 20% fluorine in argon at a fluorine rate of 0.1 mole per hour until about 1.5 moles of fluorine were added. An 8° (Centigrade) exotherm was observed during the reaction. The acidic mixture was stirred over $K_2CO_3$ until the vapors above the mixture no longer tested strongly acidic. The mixture was filtered and Freon 113 was stripped out of the filtrate, leaving 59 g. of crude product. By preparative chromatography pure 2-difluoromethyl-2-trifluoromethyl-4,4,5-trifluoro-1,3-dioxolane (12 g.) was isolated from the crude material.

Calculated for $C_5H_2F_8O_2$: F, 61.8%. Found: F, 62.2%.

This normally liquid compound has a boiling point of 101.5° C., a specific gravity of 1.65, a vapor pressure at 25° C. of 46 mm. Hg., a refractive index ($n_D^{20}$) of 1.3136, and a mild odor. It is nonflammable.

The ether starting material used in this example, i.e. 2-difluoromethyl-2-trifluoromethyl-1,3-dioxolane, can be obtained by reacting pentafluoroacetone with ethylene chlorohydrin in equimolar amounts, for example in the following manner:

SYNTHESIS OF 2-DIFLUOROMETHYL-2-TRIFLUOROMETHYL-4,4,5-TRIFLUORO-1,3-DIOXOLANE

Commercially obtained pentafluoroacetone (66 g.) was added to a solution of ethylene chlorohydrin (31 g.) in pentane (80 ml.) at 20° C. $K_2CO_3$ (35.5 g.) was added gradually, followed by stirring for 11 hours. The mixture was diluted with water, ether was added and the resultant ether-pentane layer was separated from the aqueous layer. The aqueous layer was extracted with ether and the combined organic layers were dried over anhydrous $K_2CO_3$. Ether and pentane were stripped off and pure

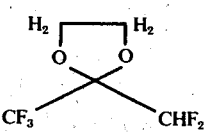

(64 g.) was obtained at 57°–59° C. under 77 mm. Hg. pressure.

b.p.: 119°
$n_D^{20}$: 1.3331

|  | C | H | F |
|---|---|---|---|
| Calculated for $C_5H_5F_5O_2$ : | 31.2 | 2.6 | 49.4 |
| Found : | 31.3 | 2.7 | 49.0 |

In order to determine the potency of the cyclic ethers of the present invention as inhalation anesthetics in combination with oxygen, tests were carried out on mice. The compounds tested were at least 99.5% pure as determined by vapor phase chromatography. In the tests, the ether compound is administered to test mice by a standard procedure in which a measured quantity of the agent is placed in a laboratory jar and allowed to completely vaporize so as to give a calculated vapor concentration. The test mice are then quickly placed in the jar and observed. Anesthesia is determined by observing the righting reflex of the mice. Recovery time is measured beginning when the mice are transferred from the test jar to room air and ending when the mice are observed to be able to walk.

In such tests the 2,2(ethylenedioxy)-3-hydroperfluorobutane just barely induced anesthesia in the mice when used at a vapor concentration of 0.2%. The period of induction was 5 minutes 57 seconds; the recovery required only 5 seconds. The mice seem sedated in recovery.

At 0.5% vapor concentration this agent induced anesthesia in 49 seconds; the induction was accompanied by moderate excitement of the animals. The mice were very sluggish in recovery, which took 6 minutes 17 seconds.

At approximately 0.6% concentration the induction time was 29 seconds and the recovery time more than 10 minutes. There was excitement in the induction, and the respiration rate fell to 60 per minute during maintenance of the anesthesia.

At 0.75% vapor concentration the induction time was 19 seconds. Respiration slowed to 50 per minute during maintenance and was slow to resume its normal rate in recovery. Recovery was not complete even after 30 minutes, and 20% of the animals were still sluggish after 24 hours.

Using 1.5% vapor concentration this agent induced anesthesia in 12 seconds. Respiration slowed progressively during maintenance, down to a rate of 20 per minute. All of the mice were cyanotic during recovery, which was slow, and 20% of them died after 20 minutes.

Using 0.5% of the other ether, 2-difluoromethyl-2-trifluoromethyl-4,4,5-trifluoro-1,3-dioxolane, required an anesthesia induction time of 4 minutes. The anesthesia was light and accompanied by spontaneous movement during maintenance. Recovery required 1 minute.

At 1.0% vapor concentration this agent induced anesthesia in 1 minute 30 seconds. Respiration was gasping and was slowed to 32 during maintenance. Color remained normal. Recovery required 3 minutes 40 seconds.

At 2.5% vapor concentration the induction required only 45 seconds. There was severe respiration depression and death of 40% of the mice during maintenance. The respiratory depression persisted during recovery, which required over 10 minutes.

While there has been described what are at present considered to be the preferred embodiments of the invention, it will be understood that various modifications may be made therein which are within the true spirit and scope of the invention.

I claim:

1. A cyclic ether compound of the formula

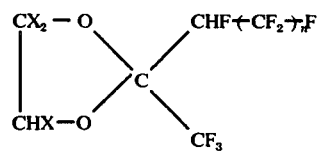

wherein $n$ is zero or one, and each X is F when $n$ is zero and is H when $n$ is one.

2. The compound of claim 1 wherein $n$ is zero and each X is F.

3. The compound of claim 1 wherein $n$ is one and each X is H.

* * * * *